United States Patent [19]
Micheli

[11] 4,289,802
[45] Sep. 15, 1981

[54] POROUS CERMET ELECTRODE AND METHOD OF MAKING SAME

[75] Inventor: Adolph L. Micheli, Mt. Clemens, Mich.

[73] Assignee: General Motors Corporation, Detroit, Mich.

[21] Appl. No.: 97,907

[22] Filed: Nov. 28, 1979

[51] Int. Cl.³ .................... C03C 15/00; G01N 27/26; G01N 27/30; B32B 3/00
[52] U.S. Cl. .................... 427/125; 156/655; 156/663; 156/656; 427/376.3; 427/376.6; 427/379; 204/195 S; 427/352
[58] Field of Search ............ 427/243, 245, 352, 372.2, 427/376.2, 379, 376.3; 156/644, 655, 663, 656; 204/195 S

[56] References Cited

U.S. PATENT DOCUMENTS

| | | | |
|---|---|---|---|
| 2,106,744 | 2/1938 | Hood | 156/663 |
| 2,834,738 | 5/1953 | Vincent | 156/663 |
| 3,113,855 | 12/1963 | Elmer | 156/663 |
| 3,485,687 | 12/1969 | Chapman | 156/644 |
| 3,578,502 | 5/1971 | Tannenberger | |
| 3,615,958 | 10/1971 | Cohen | 156/644 |
| 3,768,259 | 10/1973 | Carnahan et al. | |
| 3,914,169 | 10/1975 | Horowitz | 204/195 S |
| 3,978,006 | 8/1976 | Topp et al. | |
| 4,021,326 | 5/1977 | Pollner et al. | |
| 4,136,000 | 1/1979 | Davis et al. | 204/195 S |
| 4,169,778 | 10/1979 | Mann et al. | |

OTHER PUBLICATIONS

Rockett et al., Journal of the American Ceramic Society, v 48, n 6, pp. 329-331, Jun. 1965.

*Primary Examiner*—Ronald H. Smith
*Assistant Examiner*—Richard Bueker
*Attorney, Agent, or Firm*—Robert J. Wallace

[57] ABSTRACT

A method of making a highly porous cermet electrode on a solid electrolyte. The solid electrolyte is coated with noble metal and glass particles and heated to fuse the glass particles. The coated electrolyte is then annealed to form a separately leachable borate phase in the glass. That phase is then leached from the coating to leave a highly porous silica matrix throughout which the conductive particles are exposed.

3 Claims, No Drawings

POROUS CERMET ELECTRODE AND METHOD OF MAKING SAME

FIELD OF THE INVENTION

This invention relates to porous conductive coatings on vitreous surfaces and more particularly to a porous cermet exhaust electrode on a zirconia solid electrolyte body.

BACKGROUND OF THE INVENTION

Electrodes have been formed on zirconia solid electrolyte bodies by both thick film techniques and thin film techniques, as described in U.S. Pat. No. 4,169,778 which was issued to G. S. Mann, M. P. Murphy, D. R. Fredericks and K. R. Deming. The solid electrolyte for that sensor is in the shape of a tapered cup having inner and outer electrodes. The inner electrode can be a platinum coating applied by sintering the platinum to the zirconia, without using any appreciable bonding agent. Such a coating is highly porous but is usually not desirable for direct contact with a moving exhaust gas stream. Porous platinum coatings can be produced by sputtering techniques but the coatings are so thin that they can be abraded away by the moving exhaust gas stream. Consequently, it is known to use a porous overcoat to isolate the exhaust gas electrode from direct impingement of a moving exhaust gas stream. The sputtering of thin film platinum electrodes and the overcoating of them with a ceramic layer is described in United States patent application Ser. No. 89,264, entitled "Exhaust Electrode Process for Exhaust Gas Oxygen Sensor", filed Oct. 29, 1979 in the names of T. J. Gold, F. L. Kennard, III, P. C. Kikuchi and R. V. Wilhelm, Jr., and assigned to the assignee of this invention. Such techniques require costly equipment and a costly manufacturing environment.

Electrodes can also be made of coatings comprising powdered platinum and glass. I refer to these latter coatings as cermets. Cermets will bond well to the zirconia surface and will be quite durable with respect to erosion from the aforementioned exhaust gas stream. On the other hand, cermet coatings are not extremely porous and generally do not provide fast responding sensors.

I have found how to make a highly porous cermet coating useful as an exhaust gas electrode on a zirconia-type exhaust gas oxygen sensor. After aging, the sensors are fairly fast, e.g. less than 200 milliseconds in response time. Also, testing to the equivalent of over 40,000 km did not produce extensive electrode wear or cracking. Durability is thus apparently quite high. I further believe that my electrode is not only distinctive in its porous structure but in the manner in which it is made.

OBJECTS AND SUMMARY OF THE INVENTION

It is, therefore, an object of this invention to provide an improved cermet electrode, particularly for the exhaust electrode on an exhaust gas oxygen sensor of the solid electrolyte type. Another object of the invention is to provide an improved method of making the aforementioned porous electrode.

The invention comprehends a highly porous silica matrix bonded to a solid electrolyte and having conductive particles dispersed therewithin. The silica matrix and conductive particles comprise a porous cermet electrode on a zirconia solid electrolyte. The electrode is formed by coating a solid electrolyte with particles of metal and special glass, heating the particle coating to fuse the glass particles together and bond them to the substrate, annealing the coating to form two immiscible glass phases, one phase of which is a borate phase that is leachable from the other phase, and leaching the borate phase from the coating to retain a highly porous silica matrix throughout which the conductive particles are exposed. The special glass is made with borates of alkali and alkaline earth metals.

Other objects, features and advantages of the invention will become more apparent from the following description of preferred embodiments thereof.

DESCRIPTION OF THE PREFERRED EMBODIMENTS

In this invention conductive particles are bonded to the surface of a substrate by a unique porous glass matrix. The porous matrix is made from a unique parent glass composition. The parent glass composition can be made to separate into two immiscible phases, one of which is a borate phase that is leachable from the other phase. Such a glass composition is disclosed in U.S. Pat. No. 2,106,744 Hood et al. It involves the ternary system

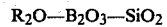

$R_2O - B_2O_3 - SiO_2$ in which R is lithium, sodium, potassium or combinations thereof. I prefer to use sodium. Compositions based on $Na_2O - 4B_2O_3 - SiO_2$ systems can be made to form two distinct phases upon proper heat treatment. One phase is almost pure silica ($SiO_2$) and the other is highly rich in $Na_2O$ and $B_2O_3$. In an acid solution the sodium oxide-boron oxide phase can be leached out, leaving a substantially silica skeletal network containing pores having a diameter of about 50–100 angstroms.

U.S. Pat. No. 2,106,744 Hood et al discloses preparing this type of glass using 3–11% sodium oxide, 29–37% boron oxide and 60–82% silicon dioxide, all percentages by weight. For purposes of this invention, I have found that a 1:4 molecular proportion of sodium oxide and boron oxide is preferred, which I refer to as sodium tetraborate. I have found that the sodium tetraborate can vary from about 33% to 75% by weight with the balance being silica ($SiO_2$). However, I may not prefer to actually use sodium tetraborate as the raw material to make the glass. Instead, the glass can be made using sodium carbonate, boric acid and fine powdered silica in appropriate proportions. The raw materials are mixed together while dry, and then heated to a temperature of about 1400° C. for two hours to melt and refine the glass. The glass is then cooled and crushed. It is then milled in alcohol to form a fine powder of approximately 200 mesh.

The powdered glass prepared in the aforementioned paragraph is then mixed with particles of an electron conductor or precursor thereof, and a liquid carrier added to form a slurry. A precursor of a noble metal particle is, itself, considered to be a noble metal particle for purposes of this invention. Any particle size normally used to make thick film inks can be used in this invention too. If desired a vehicle such as terpineol can be used instead of water as the carrier to make a thick film ink. Platinum black and/or palladium powder can be used if a catalytic electrode is desired. Palladium chloride can be used in place of palladium powder because palladium chloride decomposes to palladium metal at temperatures greater than 500° C. The ink will be subsequently fired at temperatures higher than 500° C. The particular conductor desired in the cermet should be a noble metal, to withstand the attack of the leachant used to produce electrode porosity. Accordingly, metals such as gold, silver, palladium, platinum, rhodium and alloys thereof should be used. For an exhaust electrode on a zirconia-type exhaust gas sensor, palladium provides a faster initial switching response time than platinum but is not as durable as platinum.

The ratio of metal to glass in the slurry, by weight, is about 10 parts palladium chloride to 0.7 parts glass or about 9 parts platinum to 1 part glass. In essence I like to use a slurry having sufficient metal content to provide a conductive coating as fired. In such instance, the coating should not contain much more than approximately 5–10% by weight glass. On the other hand, this conductor/glass ratio is not particularly critical. Lower ratios can be used but will have higher electrical resistance. Higher proportions can be used but may not allow as high a porosity to be formed in the resultant coating.

The glass-conductor slurry is then applied to the substrate by any convenient manner, as for example brushing, spraying, wiping, thick film printing, or the like. One or more coats may be necessary to obtain the desired coating weight, or thickness. For a catalytic electrode, a coating thickness of about 0.01–0.1 millimeter is usually desired. If one is to make an exhaust electrode for an exhaust gas oxygen sensor such as is disclosed in the aforementioned U.S. Pat. No. 4,169,778 or United States serial No. D-4,219, about 10–30 milligrams of cermet may be desired. In this latter instance the cermet is applied to the outer surface of a tapered thimble of zirconia that is partially or fully stabilized into its cubic crystalline form. On the other hand, it should be recognized that this invention would be useful on other zirconia shapes, and other solid electrolytes, such as thoria. Still further, it may be desirable to use this invention to form electrodes on other ceramic materials.

After the slurry is applied to the substrate, it can be dried by placing it in an oven at a temperature of about 100° C. for about 10 minutes. The coated substrate is then placed in a furnace which has an air atmosphere and is at room temperature. The furnace temperature is then raised to 1000° C. over a period of about 1½–2 hours. This burns away and the coated substrate is held at 1000° C. for approximately 15 minutes, and the furnace then allowed to cool to about 500° C. over a period of about 1–2 hours. From about 500° C. or lower the substrate can be cooled at essentially any rate. I prefer to leave the substrate in the furnace for another 4 or 5 hours during which it cools to about 100°–200° C. At this point I remove it from the furnace. Firing to about 1000° C. is necessary to obtain a homogeneous and intimate bond with the conductive particles and with the ceramic substrate. At this temperature, the glass is not only molten but has a low viscosity, which provides the desirable bond. After such firing, a strongly bonded but substantially gas impervious cermet coating is formed.

The coated substrate is then heated again in air to a temperature of approximately 600°–750° C. for about 16 hours. In performing this heat treatment, the substrate is placed in a room temperature furnace and the furnace heated at its normal rate to the desired heat treatment temperature. This takes about 45–90 minutes. The substrate is furnace cooled to about 100°–200° C. This heat treatment is performed to take advantage of miscibility gaps in the glass system. In other words, it separates the glass into the two distinct phases. As mentioned in the aforementioned U.S. Pat. No. 2,106,744 Hood et al, the nature of the heat treatment will have a decided bearing upon the shape, size and number of channels in which the soluble phase will form. The soluble phase is rich in sodium tetraborate. The sodium tetraborate phase is to be leached away. Hence, it is important that it be dispersed in an interconnected network, i.e. channels, rather than as globules. When the channels are leached away, they leave pores in the cermet coating. Forming channels instead of globules is not particularly difficult. They will readily form in a constant temperature heat treatment of comparatively short duration.

It appears that the glass in the cermet coating will slowly but consistently form the soluble phase at about 600°–750° C. It does not appear that it will form at all at temperatures significantly above 750° C., or fast enough below about 500° C. Even at 600°–750° C., the two phases do not immediately form. The cermet coating must be annealed, i.e. heated, for at least a few hours. Annealing for five hours at 650° C. produces a very fine-textured pattern of phases. When the soluble phase is leached out, a fine-textured high surface area glass skeleton remains. Annealing for 70 hours at 750° C. produces a coarse textured pattern of phases. In this latter instance, a lower surface area glass skeleton remains after leaching. Cermets annealed for 70 hours at 650° C. and for five hours at 750° C. yielded intermediate surface areas, with the more favorable of the two being the shorter anneal time. Hence, extremely long heat treatments, particularly at higher temperatures, will not be necessary, and probably should be avoided. They may tend to even form segregated globules of the soluble phase that cannot be leached away.

For completeness I have described a particular furnace cycle for the cermet coating firing and the subsequent anneal. However, the particular cycle used is no more critical to this invention than it is to the heating and cooling of any other ceramic material. Hence, it should be understood that other heating and cooling rates can be substituted. Analogously, I describe use of a constant temperature dwell for the glass firing and for the anneal. However, it should be understood that in some instances it may not be preferred to vary the temperature during the highest temperature portion of these cycles. Further, I describe a separate heating to bond the cermet coating to the substrate and then anneal it. Such separate heatings are believed to be unnecessary. After glass fusion at the higher temperature, as for example 900°–1100° C., one should be able to get equivalent results by then merely cooling to 600°–750° C., and then holding at the desired anneal temperature for the appropriate time. Then, one can furnace cool as usual.

The substrate is then immersed in a room temperature mineral acid, such as 10% nitric acid, 10% hydrochloric acid or 10% sulfuric acid to leach out the soluble, i.e. borate glass phase. In essence, the named acids preferentially attack the borate glass phase, and are thus referred to herein as leachants. The substrate is kept immersed in the leachant for approximately one hour, preferably with some form of agitation. It is then rinsed in distilled water and dried. The concentration of the mineral acid etchant can obviously be varied and mixtures of such acids can be used too. Incidentally, even though it is convenient to use a mineral acid etchant, it is presumed that other etchants can be found that would also work in this invention. On the other hand, fluoride-based etchants, such as hydrofluoric acid, are to be avoided because they attack the other, i.e. silica, glass phase. Analogously, I have found that for cermet coatings of about 0.02 millimeter, leaching for approximately one hour will generally etch completely through the thickness of the coating. If stronger leaching acid proportions, or thinner coatings are used, one can probably reduce leach time, and vice versa. Also, the aforementioned U.S. Pat. No. 2,106,744 Hood et al state that the type of glass in my cermet may form a continuous silica on the coating surface that must first be removed, i.e. by a hydrofluoric acid dip, before the sodium tetraborate rich phase can be leached away.

Durability of the electrode formed by this invention is quite high. Only a very thin porous overlayer at most is all that may be needed with this electrode, and perhaps none at all. If so then costs of making the electrode are reduced even further over those attendant to making it by thin film techniques, especially sputtering.

I also found that I could modify the aforementioned ternary glass system, to provide a retained phase that had a better thermal expansion match with zirconia. I added, alumina to combine with the silica, and calcium borate, Ca $B_2O_4$, to serve as a high temperature solvent for the alumina. This latter glass system was not exhaustively analyzed. However, the following composition was found to provide a miscibility gap and a leachable borate phase. It consisted of about 60% by weight of a sodium and calcium borate mixture and about 40% by weight of an equal molar silica-alumina mixture. The borate mixture was formed from 0.4 mole of $Na_2B_8O_{13}$ and 0.6 mole of Ca $B_2O_4$. The composition was vitrified at 1400° C. and ground into powder. A palladium cermet slurry was formed with this glass powder and applied as an exhaust electrode on a zirconia thimble such as previously described. The thimble was heated at 750° C. for five hours and then immersed in 10% nitric acid for one hour. A sodium-calcium borate phase was leached away, leaving a phase containing both alumina and silica. The phase retained apparently is a compound which I consider equivalent to silica for purposes of this invention. In any event, it provided a fast acting sensor as formed. It was initially believed that matching the thermal expansion characteristics of the retained glass to that of the substrate would be necessary for durability. However, microcracks that may have developed because of differences in thermal expansion between the retained glass and zirconia did not measurably affect adhesion of the film.

The embodiments of the invention in which an exclusive property or privilege is claimed are defined as follows:

1. A method of making a porous cermet electrode on a solid electrolyte substrate comprising:

coating a surface of the substrate with a slurry of noble metal particles and glass particles, the glass being annealable into an immiscible and leachable borate phase;

heating the coated substrate at a first temperature to fuse the glass and bond it to the noble metal particles and to the substrate;

heating the coated substrate at a second and lower temperature for a sufficient duration to form an interconnected network of the borate phase leachable from a second glass phase within which it is dispersed; and leaching the borate phase from the other glass phase, effective to produce a porous matrix throughout which said noble metal particles are exposed.

2. A method of making a porous cermet electrode on a solid electrolyte substrate comprising:

coating a surface of the substrate with a slurry of noble metal particles and glass particles, the glass being annealable into a silica phase and an immiscible and leachable borate phase;

heating the coated substrate to a temperature of above about 900° C. to fuse the glass and bond it to the noble metal particles and to the substrate;

annealing the coated substrate after coating fusion at a temperature of about 500°–750° C. at least a few hours to form a leachable borate glass phase dispersed within a silica phase as a reticulated network; and leaching the borate phase from the silica phase in said coating, effective to produce a highly porous silica matrix throughout which said noble metal particles are exposed.

3. A method of making a porous cermet exhaust electrode on a zirconia solid electrolyte body comprising:

coating a surface of the body with a slurry of electron conductive particles selected from the group consisting of platinum particles, palladium particles, and particles of alloys thereof, a vehicle, and glass particles, the glass being annealable into a silica phase and an immiscible and leachable borate phase;

evaporating the vehicle from the coating;

heating the coated body to a temperature of at least 1000° C. to bond the coating to the body;

then heating the coated body at a temperature of about 600°–750° C. for at least about five hours to precipitate a borate phase and a silica phase, wherein the borate phase is in the form of interconnected channels extending between major faces of the coating; and immersing the coated body in a mineral acid that selectively attacks the borate phase, whereby the borate phase is etched from the coating and a highly porous silica matrix is retained, throughout which the electron conductive particles are exposed.

* * * * *